US007105321B2

(12) United States Patent
Moeckel et al.

(10) Patent No.: US 7,105,321 B2
(45) Date of Patent: Sep. 12, 2006

(54) NUCLEOTIDE SEQUENCES WHICH CODE FOR THE CCPA2 GENE

(75) Inventors: Bettina Moeckel, Duesseldorf (DE); Caroline Kreutzer, Melle (DE); Thomas Hermann, Bielefeld (DE); Mike Farwick, Bielefeld (DE); Achim Marx, Bielefeld (DE); Walter Pfefferle, Halle (Westf.) (DE)

(73) Assignee: Degussa AG, Duesseldorf (DE)

( * ) Notice: Subject to any disclaimer, the term of this patent is extended or adjusted under 35 U.S.C. 154(b) by 286 days.

(21) Appl. No.: 10/724,827

(22) Filed: Dec. 2, 2003

(65) Prior Publication Data

US 2004/0209285 A1 Oct. 21, 2004

Related U.S. Application Data

(62) Division of application No. 09/938,642, filed on Aug. 27, 2001, now Pat. No. 6,689,586.

(30) Foreign Application Priority Data

Aug. 26, 2000 (DE) .................. 100 42 053
May 11, 2001 (DE) .................. 101 23 071

(51) Int. Cl.
C12P 13/04 (2006.01)
C12P 21/06 (2006.01)
C12P 13/06 (2006.01)
C12N 1/20 (2006.01)
C12N 15/00 (2006.01)

(52) U.S. Cl. .................. 435/106; 435/69.1; 435/115; 435/252.3; 435/252.32; 435/320.1; 536/23.1

(58) Field of Classification Search ............... 435/69.1, 435/106, 115, 252.3, 252.32, 320.1; 536/23.1
See application file for complete search history.

(56) References Cited

FOREIGN PATENT DOCUMENTS

| EP | 1108790 A2 | 6/2001 |
|---|---|---|
| WO | WO 01/00802 | 1/2001 |
| WO | WO 01/00844 | 1/2001 |
| WO | WO 01/00845 | 1/2001 |
| WO | WO 01/00847 | 1/2001 |

OTHER PUBLICATIONS

Letek et al. J Bacteriol. Jan. 2006;188(2):409-23.*
Konno et al., Accession BB350008, Jul. 12, 2000 (Alignment No. 1).
K. Mahr, et al., Database EMBL Online EBI, Acc. Nr.: AF176799, XP-002186138, pp. 1-3, "Lactobacillus Pentosus PEPQ and Catabolite Control Protein A (CCPA) Genes," Sep. 7, 1999.
T. Aleksandrzak, et al., Database EMBL Online EBI, Acc. Nr.: AF106673, XP-002186139, pp. 1-2 "Lactococcus Lactis Proline Dipeptidase (PEPQ) Gene, Catabolite Control Protein (CCPA) Gene and Thioredoxin Reductase (TRXB) Gene," Dec. 18, 1998.
K.J. Seeger, et al., Database EMBL Online EBI, Acc. Nr. AL136519, XP-002186140, pp. 1-29, "Streptomyces Coelicolor Cosmid C57A," Jan. 17, 2000.
R. Kraemer, Journal of Biotechnology, vol. 45, No. 1, pp. 1-21, "Genetic and Physiological Approaches for the Production of Amino Acids," Feb. 12, 1996.
A. Loos, et al., Applied and Environmental Microbiology, vol. 67, No. 5, pp. 2310-2318, "Development and Validation of *Corynbacterium* DNA Microarrays," May 2001.
I. Jankovic, et al., "Analysis of Catabolite Control Protein A-Dependent Repression in *Staphylococcus xylosus* by a Genomic Reporter Gene System," Journal of Bacteriology, Jan. 2001, pp. 580-586.
T.C. Patrick, et al., "Control of Lactose Transport, β-Galactosidase Activity, and Glycolysis by CcpA in *Streptococcus thermophilus*: Evidence for Carbon Catabolite Repression by a Non-Phosphoenolpyruvate-Dependent Phosphotransferase System Sugar," Journal of Bacteriology, Nov. 2000, pp. 5982-5989.
L. Muscariello, et al., "The Functional ccpA Gene is Required by Carbon Catabolite Repression in *Lactobacillus plantarum*," Applied and Environmental Microbiology, Jul. 2001, pp. 2903-2907.

* cited by examiner

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

The invention relates to polynucleotides corresponding to the ccpA2 gene and which encode a CcpA2 catabolite control protein, methods of producing L-amino acids, and methods of screening for polynucleotides which encode proteins having CcpA2 catabolite control activity.

19 Claims, 1 Drawing Sheet

Figure 1: Plasmid pCR2.1ccpA2int
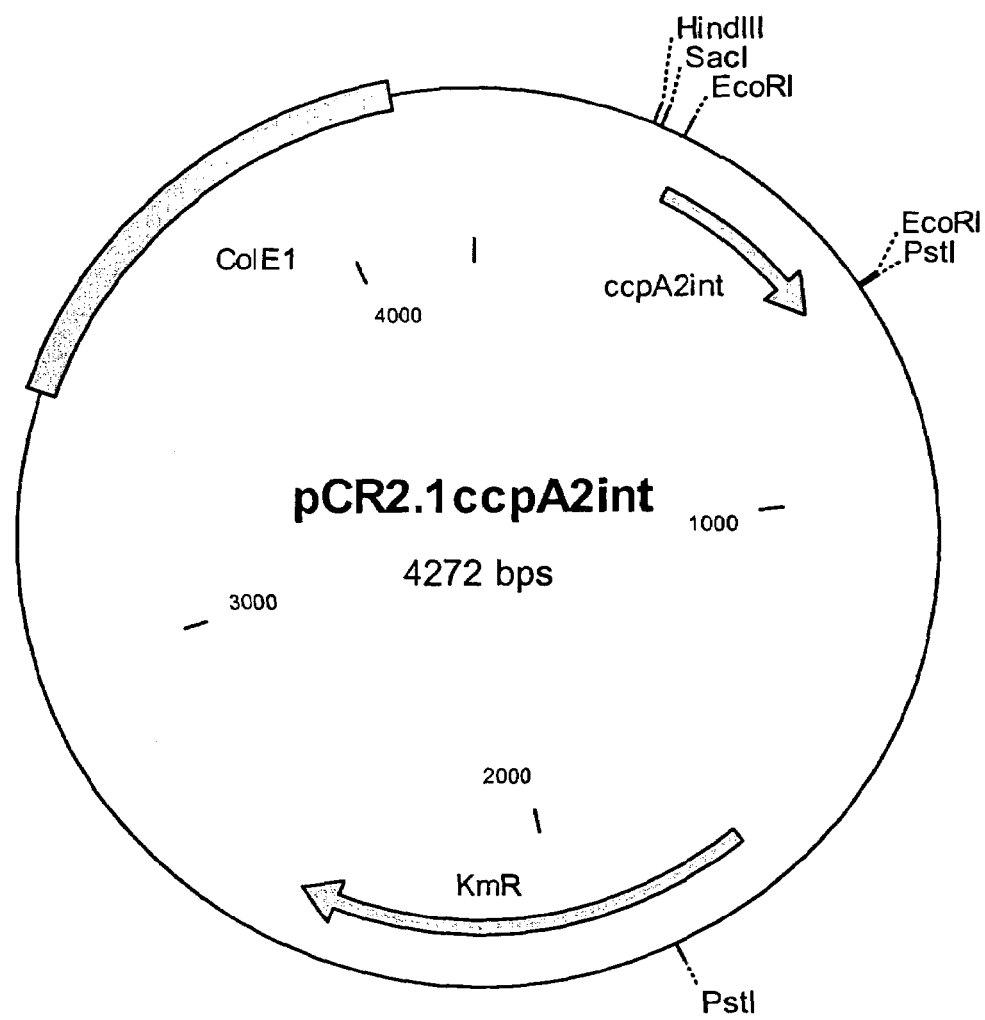

NUCLEOTIDE SEQUENCES WHICH CODE FOR THE CCPA2 GENE

CROSS-REFERENCE TO RELATED APPLICATIONS

The present application claims priority to German Application No. DE 10042053.2 filed Aug. 26, 2000 and German Application No. DE 10123071.0 filed May 11, 2001, the entire contents of both applications are incorporated herein by reference.

BACKGROUND OF THE INVENTION

1. Field of the Invention

The invention provides nucleotide sequences from *Coryneform* bacteria which code for the ccpA2 gene and a process for the fermentative preparation of amino acids, in particular L-lysine, by attenuation of the ccpA2 gene. The ccpA2 gene codes for the CcpA2 protein, which is the catabolite control protein A.

2. Discussion of the Background

L-Amino acids, particularly L-lysine, are used in human medicine and in the pharmaceuticals industry, in the foodstuffs industry and, most particularly, in animal nutrition.

It is known that amino acids are prepared by fermentation of strains of *Coryneform* bacteria, in particular *Corynebacterium glutamicum*. Because of their great importance, attempts are continuously being made to improve the preparation processes. Improvements to the process may concern measures relating to fermentation, for example, stirring and oxygen supply, or the composition of the nutrient media, such as the sugar concentration during the fermentation, or the working up to the product form by, for example, ion exchange chromatography, or the intrinsic output properties of the microorganism itself.

The output properties of these microorganisms are improved by employing methods of mutagenesis, selection and mutant selection. These methods yield strains that produce amino acids and are resistant to antimetabolites or are auxotrophic for metabolites important for regulation.

For a number of years, methods of recombinant DNA technology have also been used for improving the L-amino acid-producing strains of *Corynebacterium*. However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that attenuation of the ccpA2 gene encoding the catabolite control protein A (CcpA2) would improve L-amino acid yields.

SUMMARY OF THE INVENTION

An object of the present invention is to provide novel measures for the improved production of L-amino acids or amino acid, where these amino acids include L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan, L-arginine and the salts (monohydrochloride or sulfate) thereof.

One object of the present invention is providing a novel process for improving the fermentative production of said L-amino acids, particularly L-lysine. Such a process includes enhanced bacteria, preferably enhanced *Coryneform* bacteria, which express attenuated amounts of the CcpA2 catabolite control activity.

Thus, another object of the present invention is providing such a bacterium, which expresses an attenuated amount of CcpA2 catabolite control protein or gene products of the ccpA2 gene.

Another object of the present invention is providing a bacterium, preferably a *Coryneform* bacterium, which expresses a polypeptide that has an attenuated CcpA2 catabolite control activity.

Another object of the invention is to provide a nucleotide sequence encoding a polypeptide which has CcpA2 catabolite control protein sequence. One embodiment of such a sequence is the nucleotide sequence of SEQ ID NO: 1.

A further object of the invention is a method of making CcpA2 catabolite control protein or an isolated polypeptide having a CcpA2 catabolite control activity, as well as use of such isolated polypeptides in the production of amino acids. One embodiment of such a polypeptide is the polypeptide having the amino acid sequence of SEQ ID NO: 2.

Other objects of the invention include methods of detecting nucleic acid sequences homologous to SEQ ID NO: 1, particularly nucleic acid sequences encoding polypeptides that have CcpA2 catabolite control activity, and methods of making nucleic acids encoding such polypeptides.

The above objects highlight certain aspects of the invention. Additional objects, aspects and embodiments of the invention are found in the following detailed description of the invention.

BRIEF DESCRIPTION OF THE DRAWING

FIG. 1. Map of the plasmid pCR2.1ccpA2int.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

The invention provides an isolated polynucleotide from *Coryneform* bacteria, containing a polynucleotide sequence coding for the ccpA2 gene, selected from the group consisting of a) polynucleotide that is at least 70% identical to a polynucleotide that codes for a polypeptide containing the amino acid sequence of SEQ ID No. 2, b) polynucleotide that codes for a polypeptide containing an amino acid sequence that is at least 70% identical to the amino acid sequence of SEQ ID No. 2,
c) polynucleotide that is complementary to the polynucleotides of a) or b), and
d) polynucleotide containing at least 15 successive nucleotides of the polynucleotide sequence of a), b) or c), the polypeptide preferably having the activity of the catabolite control protein CcpA2.

The invention also provides the above-mentioned polynucleotide, preferably being a replicatable DNA containing:
(i) the nucleotide sequence shown in SEQ ID No. 1 or
(ii) at least one sequence that corresponds to sequence (i) within the range of the degeneracy of the genetic code, or
(iii) at least one sequence that hybridizes with the sequences that are complementary to sequences (i) or (ii), and optionally
(iv) sense mutations in (i) that are neutral in terms of function.

The invention also provides:
a replicatable DNA containing the nucleotide sequence as shown in SEQ ID No.1;
a polynucleotide that codes for a polypeptide containing the amino acid sequence as shown in SEQ ID No. 2;
a vector containing parts of the polynucleotide according to the invention, but at least 15 successive nucleotides (point d, supra), particularly pCR2.1ccpA2int, deposited in *Escherichia coli* DSM 14257 at the DSMZ, Braunschweig (Germany);
and *Coryneform* bacteria that contain in the ccpA2 gene an insertion or deletion, particularly using the vector pCR2.1ccpA2int.

The invention also provides polynucleotides consisting substantially of a polynucleotide sequence, which are obtainable by screening, by means of hybridization, of a corresponding *Coryneform* gene library that contains the complete gene having the polynucleotide sequence according to SEQ ID No.1, using a probe containing the sequence of said polynucleotide according to SEQ ID No.1 or a fragment thereof, and isolating said polynucleotide sequence.

Polynucleotide sequences according to the invention are suitable as hybridization probes for RNA, cDNA and DNA, in order to isolate the full length nucleic acids or polynucleotides or genes that code for the CcpA2 protein, or in order to isolate nucleic acids or polynucleotides or genes that have a high similarity with the sequence of the ccpA2 gene.

The DNA of genes that code for the CcpA2 protein can be prepared with the polymerase chain reaction (PCR) by using the polynucleotide sequences according to the invention as primers.

Such oligonucleotides acting as probes or primers contain at least 30, preferably at least 20, more preferably at least 15, consecutive nucleotides. Also suitable are oligonucleotides that have a length of at least 40 or 50 nucleotides.

"Isolated" means removed from its natural environment.

"Polynucleotide" generally refers to polyribonucleotides and polydeoxyribonucleotides. The RNA or DNA may be modified or unmodified.

The polynucleotides according to the invention include a polynucleotide shown in SEQ ID No. 1 or a fragment prepared therefrom and also those that are at least 70%, preferably at least 80% and in particular at least 90% to 95% identical to the polynucleotide according to SEQ ID No. 1 or a fragment prepared therefrom.

"Polypeptides" are understood as being peptides or proteins that comprise two or more amino acids bonded via peptide bonds.

The polypeptides according to the invention include a polypeptide shown in SEQ ID No. 2 particularly those having the biological activity of the CcpA2 protein, and also those that are at least 70%, preferably at least 80% and in particular at least 90% to 95% identical with the polypeptide shown in SEQ ID No. 2 and exhibit the mentioned activity.

The invention also provides a process for the production of amino acids, particularly L-lysine, by fermentation using *Coryneform* bacteria which, in particular, already produce amino acids and in which the nucleotide sequences coding for the ccpA2 gene are attenuated, in particular excluded or expressed at a low level.

The term "attenuation" in this connection describes the reduction or exclusion of the intracellular activity of one or more enzymes (proteins) in a microorganism which are coded by the corresponding DNA, by, for example, using a weak promoter or using a gene or allele that codes for a corresponding enzyme with a low activity, or by inactivating the corresponding gene or enzyme (protein), and optionally by combining those measures. As a result of attenuation, the activity or concentration of the corresponding protein is, in general, reduced to 0 to 50%, 0 to 25%, 0 to 10%, or 0 to 5% of the wild-type protein activity or concetration.

The term "enhancement" in this connection describes the increase in the intracellular activity of one or more enzymes in a microorganism which are coded by the corresponding DNA, by, for example, increasing the number of copies of the gene or genes, using a potent promoter or using a gene which codes for a corresponding enzyme having a high activity, and optionally combining those measures. As a result of enhancement, in particular over-expression, the activity or concentration of the corresponding protein is increased, in general, preferably ranging from at least 10%, 25%, 50%, 75%, 100%, 150%, 200%, 300%, 400%, or 500%, up to 1000% or 2000% of the wild-type protein activity or concentration present in the microorgansim.

The microorganisms provided by the present invention can prepare amino acids, in particular L-lysine, from glucose, sucrose, lactose, fructose, maltose, molasses, starch, cellulose or from glycerol and ethanol. The microorganisms can be representatives of *Coryneform* bacteria, in particular of the genus *Corynebacterium*. *Corynebacterium glutamicum* species of this genus garners special mention since it is well known to those skilled in the art for its ability to produce L-amino acids.

Suitable strains of the genus *Corynebacterium*, particularly the species *Corynebacterium glutamicum* (*C. glutamicum*), are, in particular, the known wild-type strains
*Corynebacterium glutamicum* ATCC13032
*Corynebacterium acetoglutamicum* ATCC15806
*Corynebacterium acetoacidophilum* ATCC13870
*Corynebacterium melassecola* ATCC17965,
*Corynebacterium thermoaminogenes* FERM BP-1539
*Brevibacterium flavum* ATCC 14067
*Brevibacterium lactofermentum* ATCC13869 and
*Brevibacterium divaricatum* ATCC 14020
or L-amino acid-producing mutants or strains prepared therefrom, for example, the L-lysine-producing strains
*Corynebacterium glutamicum* FERM-P 1709
*Corynebacterium glutamicum* FERM-P 6463
*Corynebacterium glutamicum* FERM-P 6464
*Corynebacterium glutamicum* DM58-1
*Corynebacterium glutamicum* DG52-5
*Corynebacterium glutamicum* DSM 5715

*Corynebacterium glutamicum* DSM 12866
*Brevibacterium flavum* FERM-P 1708 and
*Brevibacterium lactofermentum* FERM-P 1712

Preferably, a bacterial strain with attenuated expression of a ccpA2 gene that encodes a polypeptide with CcpA2 activity will improve amino acid yield at least 1%.

The inventors have succeeded in isolating the new ccpA2 gene of *C. glutamicum* that codes for the CcpA2 protein, which is a catabolite control protein A.

To isolate the ccpA2 gene or also other genes of *C. glutamicum*, a gene library of that microorganism is first prepared in *Escherichia coli* (*E. coli*). The preparation of gene libraries is described in generally known textbooks and handbooks. For example, the textbook of Winnacker: Gene und Klone, Eine Einführung in die Gentechnologie (Verlag Chemie, Weinheim, Germany, 1990) or the handbook by Sambrook et al.: Molecular Cloning, A Laboratory Manual (Cold Spring Harbor Laboratory Press, 1989). A well-known gene library is that of the *E. coli* K-12 strain W3110, which has been prepared by Kohara et al. (Cell 50, 495–508 (1987)) in λ vectors. Bathe et al. (Molecular and General Genetics, 252:255–265, 1996) describe a gene library of *C. glutamicum* ATCC13032, which was prepared with the aid of the cosmid vector SuperCos 1 (Wahl et al., 1987, Proceedings of the National Academy of Sciences, USA, 84:2160–2164) in the *E. coli* K-12 strain NM554 (Raleigh et al., 1988, Nucleic Acids Research 16:1563–1575). Börmann et al. (Molecular Microbiology 6(3), 317–326)) (1992)) in turn describe a gene library of *C. glutamicum* ATCC13032 using the cosmid pHC79 (Hohn and Collins, 1980, Gene 11, 291–298).

It is possible to use plasmids such as pBR322 (Bolivar, 1979, Life Sciences, 25, 807–818) or pUC9 (Vieira et al., 1982, Gene, 19:259–268) in order to prepare a gene library of *C. glutamicum* in *E. coli*. Suitable hosts are particularly those *E. coli* strains, which are restriction- and recombination-deficient, such as, the DH5α strain (Jeffrey H. Miller: "A Short Course in Bacterial Genetics, A Laboratory Manual and Handbook for *Escherichia coli* and Related Bacteria", Cold Spring Harbour Laboratory Press, 1992).

The long DNA fragments cloned with the aid of cosmids or other λ vectors can then be subcloned in turn into the usual vectors suitable for DNA sequencing.

Methods of DNA sequencing are described inter alia by Sanger et al. (Proceedings of the National Academy of Sciences of the United States of America USA, 74:5463–5467, (1977).

The resulting DNA sequences can then be studied using known algorithms or sequence analysis programs, such as that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

In that manner, the novel DNA sequence of *C. glutamicum* which codes for the ccpA2 gene (SEQ ID No. 1) has been obtained and forms part of this invention. Furthermore, the amino acid sequence of the corresponding protein has been derived from the present DNA sequence by the methods described above. The resulting amino acid sequence of the ccpA2 gene product is shown in SEQ ID No. 2.

Coding DNA sequences that result from SEQ ID No. 1 by the degeneracy of the genetic code also form part of the invention. In the same way, DNA sequences which hybridize with SEQ ID No. 1 or parts of SEQ ID No. 1 form part of the invention. Furthermore, to a person skilled in the art, conservative amino acid exchanges, such as exchange of glycine for alanine or of aspartic acid for glutamic acid in proteins, are known as "sense mutations." These mutations do not lead to a fundamental change in the activity of the protein, i.e. are neutral in terms of function. It is also known that changes at the N and/or C terminus of a protein may not substantially impair or may even stabilize the function thereof. The person skilled in the art will find relevant information inter alia in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences that result in a corresponding manner from SEQ ID No. 2 also form part of the invention.

Finally, DNA sequences, which are prepared by the polymerase chain reaction (PCR) using primers that result from SEQ ID No. 1 form part of the invention. Such oligonucleotides typically have a length of at least 15 nucleotides.

A person skilled in the art will find instructions for identifying DNA sequences by means of hybridization inter alia in the handbook "The DIG System Users Guide for Filter Hybridization" from Boehringer Mannheim GmbH (Mannheim, Germany, 1993) and in Liebl et al. (International Journal of Systematic Bacteriology 41: 255–260 (1991)). Hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. For reasons explained infra, the hybridization reaction is preferably carried out under a relatively low stringency compared with the washing steps (Hybaid Hybridisation Guide, Hybaid Limited, Teddington, UK, 1996).

A 5×SSC buffer at a temperature of approximately 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and subsequently 0.5×SSC (The DIG System User's Guide for Filter Hybridisation, Boehringer Mannheim, Mannheim, Germany, 1995) with a temperature of approximately 50–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise in approximately 1–2° C. increments. Commercial kits containing further instructions on hybridization are readily obtainable (e.g. DIG Easy Hyb from Roche Diagnostics GmbH, Mannheim, Germany, Catalogue No. 1603558).

A person skilled in the art will find instructions for amplification of DNA sequences with the aid of the polymerase chain reaction (PCR) inter alia in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

During work on the present invention it was found that Coryneform bacteria produce amino acids, in particular L-lysine, in an improved manner after attenuation of the ccpA2 gene.

To achieve an attenuation, either the expression of the ccpA2 gene or the catalytic properties of the enzyme protein may be diminished or excluded. The two measures may optionally be combined.

The reduction of gene expression may be effected by carrying out the culturing in a suitable manner or by genetic modification (mutation) of the signal structures of gene expression. Signal structures of gene expression are, for example, repressor genes, activator genes, operators, promoters, attenuators, ribosome binding sites, the start codon and terminators. The person skilled in the art will find information on this in the patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Patek et al. (Microbiology 142: 1297 (1996)), Vasicova et al. (Journal of Bacteriology 181: 6188 (1999)) and in known textbooks of genetics and molecular biology, such as the textbook by Knippers ("Molekulare Genetik", 6th edition, Georg Thieme Verlag, Stuttgart, Germany, 1995) or that by Winnacker ("Gene und Klone", VCH Verlagsgesellschaft, Weinheim, Germany, 1990).

Mutations that lead to a change or reduction in the catalytic properties of enzyme proteins are known from the prior art; examples that may be mentioned are the works by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus *Corynebacterium glutamicum*: Aufhebung der allosterischen Regulation und Struktur des Enzyms", Reports from the Jülich Research Centre, Jül-2906, ISSN09442952, Jülich, Germany, 1994). Summaries are found in known textbooks of genetics and molecular biology, such as that by Hagemann ("Allgemeine Genetik", Gustav Fischer Verlag, Stuttgart, 1986).

These mutations may be transitions, transversions, insertions and deletions. Depending on the effect of the amino acid exchange on the enzyme activity, "missense mutations" or "nonsense mutations" are referred to. Insertions or deletions of at least one base pair (bp) in a gene lead to frame shift mutations, as a consequence incorrect amino acids are incorporated or translation is interrupted prematurely. Deletions of several codons typically lead to a complete loss of the enzyme activity. Instructions on the production of such mutations are part of the prior art and can be found in known textbooks of genetics and molecular biology, such as the textbook by. Knippers ("Molekulare Genetik", 6th edition, Georg Thieme Verlag, Stuttgart, Germany, 1995), that by Winnacker ("Gene und Klone", VCH Verlagsgesellschaft, Weinheim, Germany, 1990) or that by Hagemann ("Allgemeine Genetik", Gustav Fischer Verlag, Stuttgart, 1986).

A common method of mutating genes of *C. glutamicum* is the method of gene disruption and gene replacement described by Schwarzer and Pühler (Bio/Technology 9, 84–87 (1991)).

In the gene disruption method, a central part of the coding region of the gene of interest is cloned in a plasmid vector that is able to replicate in a host (typically *E. coli*), but not in *C. glutamicum*. Suitable vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega corporation, Madison, Wisc., USA), pCR2.1-TOPO (Shuman Journal of Biological Chemistry 269:32678–84 (1994); U.S. Pat. No. 5,487,993), pCR®Blunt (Invitrogen, Groningen, Holland; Bernard et al., Journal of Molecular Biology, 234: 534–541 (1993)) or pEM1(Schrumpfet al, 1991, Journal of Bacteriology 173: 4510–4516). The plasmid vector containing the central part of the coding region of the gene is then transferred into the desired strain of *C. glutamicum* by conjugation or transformation. The method for conjugation is described, for example, by Schäfer et al. (Applied and Environmental Microbiology 60, 756–759 (1994)). Methods for transformation are described by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a cross-over event, the coding region of the gene in question is interrupted by the vector sequence and two incomplete alleles are obtained, one lacking the 3' end and one lacking the 5' end. This method has been used by Fitzpatrick et al. (Applied Microbiology and Biotechnology 42, 575–580 (1994)) to exclude the recA gene of *C. glutamicum*.

In the gene replacement method, a mutation, such as a deletion, insertion or base exchange, is established in vitro in the gene of interest. The allele prepared is in turn cloned in a vector that is not replicated in *C. glutamicum* and this is then transferred into the desired host of *C. glutamicum* by transformation or conjugation. After homologous recombination by means of a first cross-over event effecting integration and by means of a suitable second cross-over event effecting an excision in the target gene or in the target sequence, incorporation of the mutation or of the allele is achieved. This method was used by Peters-Wendisch et al.(Microbiology 144, 915–927 (1998)) to exclude the pyc gene of *C. glutamicum* by a deletion event.

A deletion, insertion or a base exchange can be incorporated into the ccpA2 gene in this manner.

In addition, it may be advantageous for the production of L-amino acids, in particular L-lysine, in addition to attenuation of the ccpA2 gene, to amplify, in particular to overexpress, one or more enzymes of the particular biosynthesis pathway, of glycolysis, of anaplerosis, of the citric acid cycle, of the pentose phosphate cycle or of amino acid export and optionally regulatory proteins.

Thus, for example, the preparation of L-lysine, one or more of the genes chosen from the group the lysC gene which codes for a feed-back resistant aspartate kinase (Accession No.P26512; EP-B-0387527; EP-A-0699759), the dapA gene which codes for dihydrodipicolinate synthase (EP-B 0 197 335), the eno gene which codes for enolase (DE: 19947791.4), the zwf gene which codes for the zwf gene product (JP-A-09224661), the dapD gene which codes for tetradihydrodipicolinate succinylase (Wehrmann et al., Journal of Bacteriology 180, 3159–3165 (1998)), the dapE gene which codes for succinyldiaminopimelate desuccinylase (Wehrmann et al., Journal of Bacteriology 177: 5991–5993 (1995)), the gap gene which codes for glyceraldehyde 3-phosphate dehydrogenase (Eikmanns (1992). Journal of Bacteriology 174:6076–6086), the pyc gene which codes for pyruvate carboxylase (Peters-Wendisch et al.(Microbiology 144, 915–927 (1998))

the mqo gene which codes for malate:quinone oxidoreductase (Molenaar et al., European Journal of Biochemistry 254, 395–403 (1998)), the zwal gene which codes for the Zwal protein (DE: 19959328.0, DSM 13115)

the lysE gene which codes for lysine export (DE-A-195 48 222)

may at the same time be enhanced, in particular overexpressed.

It may also be advantageous for the production of amino acids, in particular L-lysine, in addition to the attenuation of the ccpA2 gene, at the same time to attenuate one or more of the genes chosen from the group the pck gene which codes for phosphoenol pyruvate carboxykinase (DE 199 50 409.1, DSM 13047), the pgi gene which codes for glucose 6-phosphate isomerase(U.S. Ser. No. 09/396,478, DSM 12969), the poxB gene which codes for pyruvate oxidase (DE: 1995 1975.7, DSM 13114), the zwa2 gene which codes for the Zwa2 protein (DE: 19959327.2, DSM 13113).

It may also be advantageous for the production of amino acids, particularly L-lysine, in addition to attenuation of the ccpA2 gene to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms prepared according to the invention, for the purpose of production of L-amino acids, in particular L-lysine, can be cultured by batch process (continuous or discontinuous), fed batch, or repeated fed batch process. A summary of known culture methods is described in the textbook by Chmiel (Bioprozesstechnik 1. Einführung in die Bioverfahrenstechnik(Gustav Fischer Verlag, Stuttgart, 1991)) or in the textbook by Storhas (Bioreaktoren und periphere Einrichtungen(Vieweg Verlag, Braunschweig/Wiesbaden, 1994)).

A suitable culture medium must be used to meet the requirements of the particular strains. Descriptions of culture media for various microorganisms are found in the handbook "Manual of Methods for General Bacteriology" of the American Society for Bacteriology (Washington D.C., USA, 1981). Sugars and carbohydrates, (e.g., glucose, sucrose, lactose, fructose, maltose, molasses, starch and cellulose), oils and fats, (e.g., soya oil, sunflower oil, groundnut oil and coconut fat), fatty acids (e.g., palmitic acid, stearic acid and linoleic acid), alcohols (e.g., glycerol and ethanol), and organic acids (e.g., acetic acid) may be used as the carbon source. These substances may be used individually or as a mixture.

Organic nitrogen-containing compounds (e.g., peptones, yeast extract, meat extract, malt extract, corn steep liquor, soya bean flour and urea) or inorganic compounds (e.g., ammonium sulfate, ammonium chloride, ammonium phosphate, ammonium carbonate and ammonium nitrate) may be used as the nitrogen source. These substances may be used individually or as a mixture.

The phosphorus source may be phosphoric acid, potassium dihydrogen phosphate or dipotassium hydrogen phosphate (or the corresponding sodium-containing salts). Furthermore, the culture medium must comprise salts of metals (e.g., magnesium sulfate or iron sulfate), which are necessary for growth. Finally, essential growth substances, such as amino acids and vitamins, may be used in addition to the above-mentioned substances. Moreover, suitable precursors may be added to the culture medium. The starting substances mentioned may be added to the culture in the form of a single batch, or may be added in a suitable manner during fermentation.

Basic compounds (e.g., sodium hydroxide, potassium hydroxide, ammonia or aqueous ammonia) or acid compounds (e.g., phosphoric acid or sulfuric acid) may be added in a suitable manner to control the pH of the culture. Fatty acid polyglycol esters may be used to control the development of foam. In order to maintain the stability of plasmids, suitable substances having a selective action, such as antibiotics, may be added to the medium. In order to maintain aerobic conditions, oxygen or oxygen-containing gas mixtures, such as air, are introduced into the culture. The temperature of the culture is normally from 20° C. to 45° C., and preferably 25° C. to 40° C. Fermentation is continued until the maximum of the desired product has formed. This objective is normally reached within 10 hours to 160 hours.

Methods for the determination of L-amino acids are known from the prior art. The analysis can thus be carried out, for example, by anion exchange chromatography with subsequent ninhydrin derivatization as described by Spackman et al. (Analytical Chemistry, 30, 1190 (1958)) or it can be carried out by reversed phase HPLC as described by Lindroth et al. (Analytical Chemistry 51: 1167–1174 (1979)).

The process according to the invention is used for the production of amino acids, in particular L-lysin, by fermentation.

The amino acids are in general isolated by conventional processes or separated off together with constituents of the fermentation broth and optionally the entire biomass or portions thereof.

The isolation of plasmid DNA from *Escherichia coli* and all techniques of restriction, Klenow and alkaline phosphatase treatment were performed as described in Sambrook et al. (Molecular Cloning. A Laboratory Manual, 1989, Cold Spring Harbour Laboratory Press, Cold Spring Harbor, N.Y., USA). Methods for transformation of *Escherichia coli* and the composition of the usual nutrient media, such as LB or TY medium, are also described in this handbook.

The following microorganism was deposited at the Deutsche Sammlung für Mikroorganismen und Zellkulturen (DSMZ=German Collection of Microorganisms and Cell Cultures, Braunschweig, Germany) in accordance with the Budapest Treaty:

*Escherichia coli* Top10/pCR2.1ccpA2int as DSM 14257.

Having generally described this invention, a further understanding can be obtained by reference to certain specific examples which are provided herein for purposes of illustration only, and are not intended to be limiting unless otherwise specified.

EXAMPLES

Example 1

Preparation of a Genomic Cosmid Gene Library From *C. Glutamicum* ATCC 13032

Chromosomal DNA from *C. glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987), Proceedings of the National Academy of Sciences, USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA so treated was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Res. 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A Laboratory Manual, Cold Spring Harbor), the cells being plated out on LB agar (Lennox, 1955, Virology, 1:190) containing 100 mg/l ampicillin. After incubation overnight at 37° C., recombinant individual clones were selected.

Example 2

Isolation and Sequencing of the CcpA2 Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments ranging from 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the *E. coli* strain DH5αMCR (Grant, 1990, Proceedings of the National Academy of Sciences, U.S.A., 87:4645–4649) and plated out on LB agar (Lennox, 1955, Virology, 1:190) with 50 mg/l zeocin.

Plasmid preparation of the recombinant clones was carried out with the Biorobot 9600 (Product No. 900200, Qiagen, Hilden, Germany). DNA sequencing was administered by the dideoxy chain termination methodology of Sanger et al. (1977, Proceedings of the National Academies of Sciences, U.S.A., 74:5463–5467) with modifications according to Zimmermann et al. (1990, Nucleic Acids Research, 18:1067). The "RR dRhodamin Terminator Cycle Sequencing Kit" from PE Applied Biosystems(Product No. 403044, Weiterstadt, Germany) was used. Separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analyses were prepared with the XNIP program (Staden, 1986, Nucleic Acids Research, 14:217–231). Further analyses were carried out with the "BLAST search program" (Altschul et al., 1997, Nucleic Acids Research, 25:3389–3402) against the non-redundant databank of the "National Center for Biotechnology Information" (NCBI, Bethesda, Md., USA).

The resulting nucleotide sequence is shown in SEQ ID No. 1. Analysis of this nucleotide sequence revealed an open reading frame of 1041 bp, which was designated the ccpA2 gene. The ccpA2 gene codes for a polypeptide of 346 anino acids (SEQ ID No. 2).

Example 3

Preparation of an Integration Vector for Integration Mutagenesis of the CcpA2 Gene From the *C. glutamicum* ATCC strain 13032, chromosomal DNA was isolated by the method of Eikmanns et al. (Microbiology 140: 1817–1828 (1994)). On the basis of the sequence of the ccpA2 gene known for *C. glutamicum* from Example 2, the following oligonucleotides were objectively designed for the polymerase chain reaction:

```
ccpA2intA (SEQ ID NO. 3):
5'AGA GCT GCT TGG TCA GAC TT 3' ccpA2intB (SEQ ID NO. 4):
5'ATC CAG ATT CTT GGC GGT AG 3'
```

The primers shown were synthesized by MWG Biotech (Ebersberg, Germany) and the PCR reaction was carried out by the standard PCR method of Innis et al. (PCR protocols. A guide to methods and applications, 1990, Academic Press) with Pwo-Polymerase from Boehringer. With the aid of the polymerase chain reaction, an 322 bp internal fragment of the ccpA2 gene (SEQ ID No. 1) was isolated.

The amplified DNA fragment was ligated into the vector pCR2.1-TOPO (Mead at al. (1991), Bio/Technology 9:657–663) with the TOPO TA Cloning Kit from Invitrogen Corporation (Carlsbad, Calif., USA; Catalogue Number K4500-01).

The *E. coli* strain TOP10F was then transformed with the ligation batch (Hanahan, Ind.: DNA cloning. A practical approach. Vol. 1, IRL-Press, Oxford, Washington D.C., USA 1985). Selection for plasmid-carrying cells was made by plating out the transformation batch on LB agar (Sambrook et al., Molecular Cloning: A Laboratory Manual. $2^{nd}$ Ed., Cold Spring Harbor Laboratory Press, Cold Spring Harbor, N.Y., 1989), which had been supplemented with 25 mg/l kanamycin. Plasmid DNA was isolated from a transformant with the aid of the QIAprep Spin Miniprep Kit from Qiagen and tested by restriction with the restriction enzyme EcoRI and subsequent agarose gel electrophoresis (0.8%). The plasmid was designated pCR2.1ccpA2int (FIG. 1). The abbreviations and designations used in FIG. 1 have the following meaning.

| | |
|---|---|
| KmR: | Kanamycin resistance gene |
| EcoRI: | Cleavage site of the restriction enzyme EcoRI |
| HindIII: | Cleavage site of the restriction enzyme HindIII |
| SacI: | Cleavage site of the restriction enzyme SacI |
| PstI: | Cleavage site of the restriction enzyme PstI |
| ccpA2int: | Internal fragment of the ccpA2 gene |
| ColE1 ori: | Replication origin of the plasmid ColE1 |

Example 4

Integration Mutagenesis of the CcpA2 Gene in the Lysine Producer DSM 5715

The vector pCR2.1ccpA2int mentioned in Example 3 was introduced into *C. glutamicum* DSM 5715 (EP 435 132) by the electroporation method of Tauch et al. (FEMS Microbiological Letters, 123:343–347 (1994)). Strain DSM 5715 is an AEC-resistant lysine producer. The vector pCR2.1ccpA2int is unable to replicate independently in DSM 5715 and is retained in the cell only if it has been integrated into the chromosome of DSM 5715. Selection of clones with pCR2.1ccpA2int integrated into the chromosome was performed by plating out the electroporation batch on LB agar (Sambrook et al., Molecular Cloning: A Laboratory Manual. $2^{nd}$ Ed., Cold Spring Harbor Laboratory Press, Cold Spring Harbor, N.Y.), which had been supplemented with 15 mg/l kanamycin.

For detection of the integration, the ccpA2int fragment was labelled with the Dig hybridization kit from Boehringer by the method of "The DIG System Users Guide for Filter Hybridization" of Boehringer Mannheim GmbH (Mannheim, Germany, 1993). Chromosomal DNA of a potential integrant was isolated by the method of Eikmanns et al. (Microbiology 140: 1817–1828 (1994)) and in each case cleaved with the restriction enzymes SalI, SacI and HindIII. The fragments formed were separated by agarose gel electrophoresis and hybridized at 68° C. with the Dig hybridization kit from Boehringer. The plasmid pCR2.1ccpA2int mentioned in Example 3 had been inserted into the chromosome of DSM 5715 within the chromosomal ccpA2 gene. The strain was called DSM 5715::pCR2.1ccpA2int.

Example 5

Preparation of L-lysine

The *C. glutamicum* strain DSM 5715::pCR2.1ccpA2int obtained in Example 4 was cultured in a nutrient medium suitable for the production of L-lysine by fermentation, and the L-lysine content in the culture supernatant was determined.

To that end, the strain was first incubated on an agar plate with the corresponding antibiotic (brain-heart agar with 25 mg/l kanamycin) for 24 hours at 33° C. A pre-culture was inoculated (10 ml medium in a 100 ml conical flask). The complete CgIII medium was used as the medium for the pre-culture starting from this agar plate culture.

| Cg III Medium | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to the pre-culture medium. The pre-culture was then incubated for 16 hours at 33° C. at 240 rpm on a shaker. A main culture was inoculated from this pre-culture so that the initial OD (660 nm) of the main culture was 0.1 OD. MM medium was used for the main culture.

| MM Medium | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7H_2O$ | 1.0 g/l |
| $CaCl_2 * 2H_2O$ | 10 mg/l |
| $FeSO_4 * 7H_2O$ | 10 mg/l |
| $MnSO_4 * H_2O$ | 5.0 mg/l |
| Biotin (sterile-filtered) | 0.3 mg/l |
| Thiamine*HCl (sterile-filtered) | 0.2 mg/l |
| Leucine (sterile-filtered) | 0.1 g/l |
| $CaCO_3$ | 25 g/l |

CSL, MOPS and the salt solution are adjusted to pH 7 with aqueous ammonia and autoclaved. The sterile substrate and vitamin solutions are then added, as well as the dry, autoclaved $CaCO_3$.

Cell growth was carried out in a 10 ml volume in a 100 ml conical flask with baffles. Kanamycin (25 mg/l) was added. Cell growth was carried out at 33° C. and 80% atmospheric humidity.

After 72 hours, the OD was determined at a measurement wavelength of 660 nm with a Biomek 1000 (Beckmann Instruments GmbH, Munich). The amount of L-lysine formed was determined with an amino acid analyzer from Eppendorf-BioTronik (Hamburg, Germany) by ion-exchange chromatography and post-column derivatization with ninhydrin detection.

The result of the experiment is shown in Table 1.

TABLE 1

| Strain | OD (660 nm) | Lysine HCl g/l |
|---|---|---|
| DSM 5715 | 7.9 | 13.53 |
| DSM 5715::pCR2.1ccpA2int | 8.1 | 14.94 |

Obviously, numerous modifications and variations on the present invention are possible in light of the above teachings. It is therefore to be understood that within the scope of the appended claims, the invention may be practiced otherwise than as specifically described herein.

What is claimed is:

1. A process for producing an L-amino acid comprising:
   culturing a bacterial cell in a medium suitable for producing L-amino acid, and
   recovering or isolating said L-amino acid,
   wherein said bacterial cell has been modified to eliminate or reduce the expression of the CcpA2 polypeptide compared to the corresponding unmodified bacterium, and
   wherein said CcpA2 polypeptide exhibits catabolite control activity and is encoded by a polynucleotide which is at least 95% identical to SEQ ID NO: 1.

2. The process of claim 1, wherein said bacterial cell is a *coryneform* bacterium.

3. The process of claim 2, wherein said bacterial cell is selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum,* and *Brevibacterium divaricatum*.

4. The process of claim 1, wherein the CcpA2 polypeptide comprises SEQ ID NO: 2.

5. The process of claim 1, wherein the L-amino acid is L-lysine.

6. The process of claim 1, wherein the L-amino acid is not L-lysine.

7. The process of claim 1, wherein the expression of the CcpA2 polypeptide has been eliminated.

8. The process of claim 1, wherein the expression of the CcpA2 polypeptide has been attenuated.

9. The process of claim 1, wherein the expression of the CcpA2 polypeptide has been attenuated by genetic modification of a signal structure involved in expression of the CcpA2 coding sequence.

10. The process of claim 1, wherein the expression of the CcpA2 polypeptide has been eliminated or attenuated by modification of the CcpA2 coding sequence.

11. The process of claim 1, wherein said bacterium contains one or more coding sequences from lysC, dapA, eno, zwf, dapD, dapE, gap, pyc, mqo, zal, or lysE, wherein said one or more coding sequences is over-expressed compared to a corresponding unmodified bacterium.

12. The process of claim 1, wherein said bacterium has had one or more coding sequences from pck, pgi, poxB, or zwa2 eliminated or attenuated compared to a corresponding unmodified strain.

13. The process of claim 1, wherein said L-amino acid is produced by a batch fermentation process.

14. The process of claim 1, wherein said L-amino acid is produced by a fed batch fermentation process.

15. The process of claim 1, wherein said L-amino acid is produced by a repeated fed fermentation process.

16. The process of claim 1, wherein said L-amino acid is recovered from the culture medium.

17. The process of claim 1, wherein said L-amino acid is recovered along with at least a portion of the biomass of the culture medium.

18. A process for producing an L-amino acid comprising:
culturing a bacterial cell in a medium suitable for producing an L-amino acid, and
recovering or isolating said L-amino acid;
wherein said bacterial cell has been modified to eliminate or reduce the expression of the CcpA2 polypeptide compared to the corresponding unmodified bacterium, and
wherein said CcpA2 polypeptide is encoded by a polynucleotide which may be obtained from *Brevibacterium* or *Corynebacterium* by PCR using the oligonucleotides of SEQ ID NOS: 3 and 4.

19. The process of claim 1, wherein said CcpA2 polypeptide is encoded by a polynucleotide which comprises nucleotides 241 to 1278 of SEQ ID NO: 1.

* * * * *

SEQUENCE LISTING

<160> NUMBER OF SEQ ID NOS: 4

<210> SEQ ID NO 1
<211> LENGTH: 1500
<212> TYPE: DNA
<213> ORGANISM: Corynebacterium glutamicum
<220> FEATURE:
<221> NAME/KEY: CDS
<222> LOCATION: (241)..(1278)
<223> OTHER INFORMATION:

<400> SEQUENCE: 1

```
caagggttgt ggatgaacct accccgtgag actccataag taccccatac tttgcccgac      60
gtctcatgaa gtgcggtttt aaatcattag ccttcttatt cacttcccgg gatcaccacc     120
cccacttcct acccctgttg ccaacatcgc cttgcacgta ataggttaaa acacaagtga     180
atgtaatcgt ttgcagcaat cgattacata aggtagata atgagataaa gcgaggcgct     240 atg gcg acg gaa aaa ttc cga ccg act ctt aaa gat gtc gct cgt caa      288
Met Ala Thr Glu Lys Phe Arg Pro Thr Leu Lys Asp Val Ala Arg Gln
1               5                   10                  15 gca ggt gtc tcc atc gcc aca gca tca cga gca cta gcg gat aat ccg      336
Ala Gly Val Ser Ile Ala Thr Ala Ser Arg Ala Leu Ala Asp Asn Pro
                20                  25                  30 gcg gtt gct gca tcg act cgt gaa aga atc caa caa tta gcc tct gat      384
Ala Val Ala Ala Ser Thr Arg Glu Arg Ile Gln Gln Leu Ala Ser Asp
            35                  40                  45 ctg ggt tac cgg gcc aat gct caa gct cgt gcg ctt cgc agt tct cgc      432
Leu Gly Tyr Arg Ala Asn Ala Gln Ala Arg Ala Leu Arg Ser Ser Arg
        50                  55                  60 agc aac acc att ggt gtg att gtt ccc agt ttg att aac cat tac ttc      480
Ser Asn Thr Ile Gly Val Ile Val Pro Ser Leu Ile Asn His Tyr Phe
65                  70                  75                  80 gcc gca atg gtt act gaa att caa agc acc gcc agc aaa gct gga ctt      528
Ala Ala Met Val Thr Glu Ile Gln Ser Thr Ala Ser Lys Ala Gly Leu
                85                  90                  95 gcc acg att atc acc aac agc aat gaa gat gcg acc act atg tct ggg      576
Ala Thr Ile Ile Thr Asn Ser Asn Glu Asp Ala Thr Thr Met Ser Gly
            100                 105                 110 tct ttg gag ttt ctc acc tcg cat ggt gtc gat gga atc atc tgc gta      624
Ser Leu Glu Phe Leu Thr Ser His Gly Val Asp Gly Ile Ile Cys Val
        115                 120                 125 cct aat gag gaa tgc gcg aat caa cta gag gac ttg cag aag caa gga      672
Pro Asn Glu Glu Cys Ala Asn Gln Leu Glu Asp Leu Gln Lys Gln Gly
130                 135                 140 atg cca gtg gtg ttg gtt gac cga gag ctt cca gga gac tcc acc atc      720
Met Pro Val Val Leu Val Asp Arg Glu Leu Pro Gly Asp Ser Thr Ile
145                 150                 155                 160 cca acg gcg acc tct aac ccc caa cca gga atc gcc gca gca gta gaa      768
Pro Thr Ala Thr Ser Asn Pro Gln Pro Gly Ile Ala Ala Ala Val Glu
                165                 170                 175 ctc ctg gct cac aac aac gcg ttg ccg att ggt tac ctc tca ggt ccc      816
Leu Leu Ala His Asn Asn Ala Leu Pro Ile Gly Tyr Leu Ser Gly Pro
            180                 185                 190 atg gac acc tca aca ggt aga gag cga tta gag gat ttc aaa gca gcc      864
Met Asp Thr Ser Thr Gly Arg Glu Arg Leu Glu Asp Phe Lys Ala Ala
        195                 200                 205 tgc gcc aac tcc aaa att ggc gaa cag ctc gtt ttt ctg ggt ggg tac      912
Cys Ala Asn Ser Lys Ile Gly Glu Gln Leu Val Phe Leu Gly Gly Tyr
210                 215                 220
```

-continued

```
gaa caa agc gtt gga ttt gaa ggc gct acg aaa ttg ctc gat caa gga      960
Glu Gln Ser Val Gly Phe Glu Gly Ala Thr Lys Leu Leu Asp Gln Gly
225                 230                 235                 240 gct aaa act ctt ttt gcc ggc gat tct atg atg acg atc ggt gtc att     1008
Ala Lys Thr Leu Phe Ala Gly Asp Ser Met Met Thr Ile Gly Val Ile
            245                 250                 255 gaa gcc tgc cat aag gct ggt ttg gtt atc ggc aag gat gtc agc gtg     1056
Glu Ala Cys His Lys Ala Gly Leu Val Ile Gly Lys Asp Val Ser Val
        260                 265                 270 att ggt ttt gat aca cat ccg ctt ttt gcc ctg caa cct cat ccg ttg     1104
Ile Gly Phe Asp Thr His Pro Leu Phe Ala Leu Gln Pro His Pro Leu
    275                 280                 285 aca gtg att gat caa aat gta gaa caa cta gcc caa cga gca gtg tct     1152
Thr Val Ile Asp Gln Asn Val Glu Gln Leu Ala Gln Arg Ala Val Ser
290                 295                 300 atc ctc acc gaa tta att gca ggc acg gta cct agc gtg acg aaa act     1200
Ile Leu Thr Glu Leu Ile Ala Gly Thr Val Pro Ser Val Thr Lys Thr
305                 310                 315                 320 acg atc ccc act gcc ctt att cat cgt gaa tca atc atc aac tcc act     1248
Thr Ile Pro Thr Ala Leu Ile His Arg Glu Ser Ile Ile Asn Ser Thr
                325                 330                 335 tta agg aag aag gat gga ctc ccc aat gag taactcaacc ggtaccgaca       1298
Leu Arg Lys Lys Asp Gly Leu Pro Asn Glu
            340                 345 ttgtcgttgt cggatccatc aatgccgatc tcaccgcaaa agttcaacgc caccctgaac   1358
ctggagaaac cctcctgggt agcggcggca cagtgagtgc tggtggcaaa ggcgccaacc   1418
aagctgtggc ggcagcgcaa ttaggtgcca aagtcaccat gatcggtgcg gtcggaaccg   1478
atcaaatggc tggcgaggcg ct                                            1500

<210> SEQ ID NO 2
<211> LENGTH: 346
<212> TYPE: PRT
<213> ORGANISM: Corynebacterium glutamicum

<400> SEQUENCE: 2

Met Ala Thr Glu Lys Phe Arg Pro Thr Leu Lys Asp Val Ala Arg Gln
1               5                   10                  15

Ala Gly Val Ser Ile Ala Thr Ala Ser Arg Ala Leu Ala Asp Asn Pro
            20                  25                  30

Ala Val Ala Ala Ser Thr Arg Glu Arg Ile Gln Gln Leu Ala Ser Asp
        35                  40                  45

Leu Gly Tyr Arg Ala Asn Ala Gln Ala Arg Ala Leu Arg Ser Ser Arg
    50                  55                  60

Ser Asn Thr Ile Gly Val Ile Val Pro Ser Leu Ile Asn His Tyr Phe
65                  70                  75                  80

Ala Ala Met Val Thr Glu Ile Gln Ser Thr Ala Ser Lys Ala Gly Leu
                85                  90                  95

Ala Thr Ile Ile Thr Asn Ser Asn Glu Asp Ala Thr Thr Met Ser Gly
            100                 105                 110

Ser Leu Glu Phe Leu Thr Ser His Gly Val Asp Gly Ile Ile Cys Val
        115                 120                 125

Pro Asn Glu Glu Cys Ala Asn Gln Leu Glu Asp Gln Lys Gln Gly
    130                 135                 140

Met Pro Val Val Leu Val Asp Arg Glu Leu Pro Gly Asp Ser Thr Ile
145                 150                 155                 160
```

-continued

```
Pro Thr Ala Thr Ser Asn Pro Gln Pro Gly Ile Ala Ala Ala Val Glu
            165                 170                 175

Leu Leu Ala His Asn Asn Ala Leu Pro Ile Gly Tyr Leu Ser Gly Pro
            180                 185                 190

Met Asp Thr Ser Thr Gly Arg Glu Arg Leu Glu Asp Phe Lys Ala Ala
            195                 200                 205

Cys Ala Asn Ser Lys Ile Gly Glu Gln Leu Val Phe Leu Gly Gly Tyr
            210                 215                 220

Glu Gln Ser Val Gly Phe Glu Gly Ala Thr Lys Leu Leu Asp Gln Gly
225                 230                 235                 240

Ala Lys Thr Leu Phe Ala Gly Asp Ser Met Met Thr Ile Gly Val Ile
            245                 250                 255

Glu Ala Cys His Lys Ala Gly Leu Val Ile Gly Lys Asp Val Ser Val
            260                 265                 270

Ile Gly Phe Asp Thr His Pro Leu Phe Ala Leu Gln Pro His Pro Leu
            275                 280                 285

Thr Val Ile Asp Gln Asn Val Glu Gln Leu Ala Gln Arg Ala Val Ser
290                 295                 300

Ile Leu Thr Glu Leu Ile Ala Gly Thr Val Pro Ser Val Thr Lys Thr
305                 310                 315                 320

Thr Ile Pro Thr Ala Leu Ile His Arg Glu Ser Ile Ile Asn Ser Thr
            325                 330                 335

Leu Arg Lys Lys Asp Gly Leu Pro Asn Glu
            340                 345

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA

<400> SEQUENCE: 3
agagctgctt ggtcagactt                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
atccagattc ttggcggtag                                                    20
```